United States Patent [19]
Van den Neste et al.

[11] Patent Number: 6,096,104
[45] Date of Patent: Aug. 1, 2000

[54] MIXED ORGANOMETALLIC COMPOSITIONS INCLUDING AT LEAST THREE METALS, AND USES THEREOF AS FUEL ADDITIVES

[75] Inventors: Corinne Van den Neste; Jean Peyrot, both of Le Havre; Guy Brisset, Saint-Just; Gerard Briard, Vernon, all of France

[73] Assignees: Total Raffinage Distribution S.A., Puteaux; Gamlen Industries S.A., Bougival, both of France

[21] Appl. No.: 09/230,546

[22] PCT Filed: Jul. 23, 1997

[86] PCT No.: PCT/FR97/01369

§ 371 Date: Apr. 27, 1999

§ 102(e) Date: Apr. 27, 1999

[87] PCT Pub. No.: WO98/04655

PCT Pub. Date: Feb. 5, 1998

[30] Foreign Application Priority Data

Jul. 29, 1996 [FR] France ................................ 96 09517

[51] Int. Cl.[7] ........................................................ C10L 1/30
[52] U.S. Cl. ................................. 44/363; 44/364; 44/365
[58] Field of Search ................................ 44/363, 364, 365

[56] References Cited

U.S. PATENT DOCUMENTS

| | | | |
|---|---|---|---|
| 4,568,360 | 2/1986 | Bresset et al. | 44/363 |
| 4,675,027 | 6/1987 | Chibnik | 44/363 |
| 5,145,488 | 9/1992 | Weber et al. | 44/363 |
| 5,461,172 | 10/1995 | Cells | 44/363 |

FOREIGN PATENT DOCUMENTS

| | | |
|---|---|---|
| 112 219 | 6/1984 | European Pat. Off. . |
| 426 978 | 5/1991 | European Pat. Off. . |
| 1 325 217 | 7/1963 | France . |
| 2 632 966 | 12/1989 | France . |
| 40 32 845 | 7/1991 | Germany . |
| 2 091 291 | 7/1982 | United Kingdom . |
| 2 248 068 | 3/1992 | United Kingdom . |
| WO 87/00193 | 1/1987 | WIPO . |
| WO 95/18198 | 7/1995 | WIPO . |

OTHER PUBLICATIONS

Derwent, Japan 05 076 762, XP 002030019, Mar. 1993, Abstract.

Primary Examiner—Jacqueline V. Howard
Attorney, Agent, or Firm—Sughrue, Mion, Zinn Macpeak & Seas, PLLC

[57] ABSTRACT

Compositions including at least three metals (M1, M2, M3) are disclosed. The first metal (M1) is at least one metal selected from the iron group or the manganese group, and is preferably selected from iron, manganese, cobalt and nickel. The second metal (M2) is at least one metal selected from the rare earth group and is preferably selected from cerium, lanthanum, neodymium and praseodymiium. The third metal (M3) is selected from the group of alkaline or alkaline-earth metals, and is preferably selected from barium, strontium, calcium and lithium. The weight ratio (R) of metal (M3) to metal (M2) is greater than 0.15, and preferably greater than 1.5.

32 Claims, 2 Drawing Sheets

MIXED ORGANOMETALLIC COMPOSITIONS INCLUDING AT LEAST THREE METALS, AND USES THEREOF AS FUEL ADDITIVES

This application is a 371 of PCT/FR/97/01369, Jul. 23, 1997.

This invention relates to mixed organometallic compositions, containing at least three metals belonging respectively to the manganese or iron group, the rare earth group, and the alkaline or alkaline earth group. It also relates to applications of these organometallic compositions as fuel additives for hydrocarbonic liquid fuels or motor fuels, such as fuel oil and diesel fuel.

We are already aware of the use of organic acid organo-metallic or organo-metalloid complex salts as combustion additives to hydrocarbonic liquid fuels, for example, to ease and improve the combustion of these fuels. Such additives are, for example, composed of a complex salt obtained from an organic acid (fatty acids with more than 7 carbon atoms) and iron (see FR-A-2 172 797), or manganese (see FR-A-2 486 083), or rare earth metals, in particular cerium (see FR-A-2 359 192). The applicants have also proposed mixed combustion additives containing iron and cerium (see EP-A-1 12 219).

The mechanism of action of these additives on the combustion, in particular, of a fuel oil seems relatively well known: the metallic oxides contained in the additive would adsorb on the asphaltenes always present in a fuel oil and, because of their catalytic effect on the combustion of these asphaltenes, these metallic oxides would thus reduce the quantity of solid unburned components released during the combustion.

However, because of the actual rarity of the components, the use of compounds with a rare earth base is costly. Therefore, to reduce the cost, many substitute organometallic compounds have also been researched and tested by the applicants, without much success.

Nevertheless, surprisingly so, it was found that not only can the content in rare earths be considerably reduced by the adjunction of a third metal of the alkaline and or alkaline earth type, but also, the quality of these additives is considerably improved.

The applicants have thus established that, surprisingly so, the adjunction of a third element along side the iron and cerium allows, not only to improve on the qualities of combustion as far as the environment is concerned, in particular in an urban area—as these combustion qualities are subject to regulations that are more and more strict—but also to reduce the cost of the additive.

The purpose of this invention is therefore to propose mixed organometallic compositions that contain at least three metals, whose efficiency as a combustion adjuvant is at least the same as the rare earth and iron salts mixtures with an identical overall metal content, and whose cost, due to the reduction of the rare earth content, is significantly reduced in relation to these same salts.

The object of this invention is therefore mixed organometallic compositions, characterized by the fact that they contain organic acid salts of at least three metals M1, M2 and M3, the first metal, M1, being composed of at least one metal belonging either to the iron group or the manganese group, preferably a metal chosen from among iron, manganese or nickel, the second metal, M2, being composed of al least one metal belonging to the rare earth group, preferably a metal chosen from among cerium, lanthanum, neodymium or praseodymium, the third metal, M3, being chosen from among the alkaline or alkaline earth metal group, preferably, a metal chosen from among barium, strontium, calcium or lithium, and by the fact that the R ratio of the mass contents of the M3/M2 metals, is greater than 0.15, preferably greater than 1.5.

Indeed, it has been proved that the addition of a third element to the composition, belonging to the alkaline or alkaline earth metal group, makes it possible to unexpectedly reduce, on the one hand, the additive's content of rare earth, and on the other hand, the level of the quantity of solid unburned components produced during the combustion of a fuel oil containing said composition as an additive. Furthermore, for an identical overall metal content in the composition, the use of calcium in this composition makes it possible to reduce by such amount the quantity or rare earth necessary and therefore to reduce the cost of the additive.

In the description of the object of the invention, and for the remainder of this description, for the M1 metal chosen from among the iron or manganese groups, iron, because of its low cost, is the preferred element. It can be used alone or mixed with manganese, cobalt or nickel.

In the same manner, the M2 metal chosen from among the rare earth metals is preferably cerium. It can be used either alone or mixed with lanthanum, neodymium or praseodymium.

The preferred element for the M3 metal belonging to the alkaline or alkaline earth group is calcium, which can be used either alone or mixed with lithium, strontium or barium.

The organometallic derivatives of the iron or the manganese group and the rare earth group can be prepared according to the methods described in the prior art, in particular in the European patent EP-B-112 219, filed in the name of the applicants, thus making it possible to obtain solutions highly concentrated in metal and greatly exceeding the normal stoichiometric values.

The solution containing the calcium can be obtained from a hydro-soluble salt, an oxide or a hydroxide and a fatty acid containing, preferably, more than 7 carbon atoms. Other organic acids can also be used such as, for example, alkyl-, aryl- or alkylarylsulfonic acids and carboxylic acids with an alkylaryl chain containing, preferably, more than 8 carbon atoms.

The final composition can then be obtained by mixing the solutions, in particular the iron, cerium and calcium solutions, in an organic solvent, preferably of the aromatic type, and whose content in aromatic compounds is greater than 50% and preferably greater than 80%. The product obtained is stable and fluid at room temperature, which allows for great ease of implementation.

Preferably, the compositions as set forth in the invention contain a content in M1 metal of the iron or manganese groups greater than or equal to 30% by weight, in relation to the total weight of the metals, and a content in M2 rare earth metal greater than or equal to 10% by weight. The content in M3 metal belonging to the alkaline or alkaline earth group is directly tied to the content in M2 rare earth metal by the ratio R of mass contents of the M3 and M2 metals which must be greater than 0.15 and, preferably, greater than 1.5.

These compositions are soluble in hydrocarbons and therefore can be added in adequate percentages to the hydrocarbonic liquid fuels and motor fuels such as heavy, light or domestic residual fuel oils, and gas oils, in such a way that said fuels or motor fuels contain between 10 and 100 ppm of added metals, and preferably, between 40 and 100 ppm.

The use of such an additive, with the contents as indicated above, in a fuel makes it possible to reduce the emission of solid unburned components and therefore to respect the regulations in force. It also authorizes the operation of the heating plant with less excess air than in the traditional conditions; thus the trimetallic additive allows for the indirect reduction of the emission of nitrogen oxides.

The performance of the combustion plants is also improved by:

- an operation with less excess air,
- a reduction of the loss in smoke of solid unburned components,
- less clogging of the exchange surfaces.

Lastly, the operating cost will be minimized by a greater mean time between sweepings, cleanings and in particular, disposals on land of soot, collected for example, on the dust collectors.

The following example is intended to illustrate the invention in a non restrictive manner.

BRIEF DESCRIPTION OF DRAWINGS

In this example, we will refer to the attached drawings, of which

EXAMPLE

Figure 1:
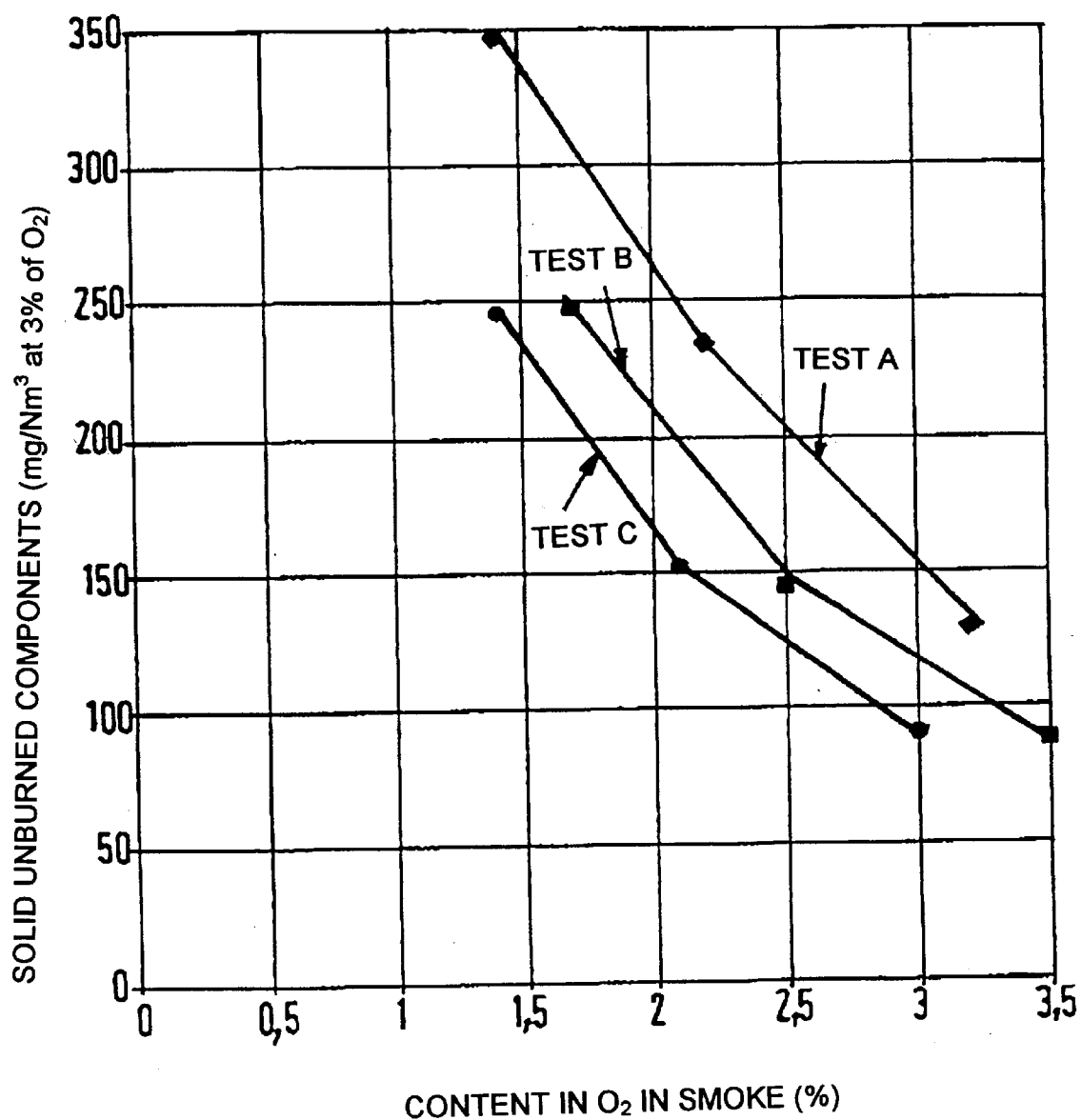
FIGS. 1 and 2 are graphs that illustrating the results of tests completed in the conditions that will be described in this example.

We successively feed a boiler with the same liquid fuel, without any additives for the first test (test A), then with the addition of a composition containing at least two metals (iron and cerium) as described in the patent EP-B-112 219 filed in the names of the applicants (test B), and lastly containing the trimetallic additive that is the object of this invention (test C).

The injection of the additives in the liquid fuel is carried out using a metering pump at the level of the heating device. The quantities of additive introduced in the fuel are such that the total content in metal added to the fuel by said additives is of 40 ppm (expressed in relation to the total weight of the fuel and the additive).

Each test is carried out at three levels of excess air that vary by approximately 3% to approximately 1.5% of oxygen in the smoke.

The boiler is a smoke-water tube type boiler, with the following characteristics:

furnace power: 7000 th/h, furnace diameter: 1200 mm, furnace length: 4920 mm, burner: nominal fuel flow of 550 Kg/h with an angle of diffusion of 70° C. and an atomization realized by compressed air at $6.10^5$ Pa (6 bars).

The liquid fuel used for each test is a heavy fuel oil, whose main physicochemical characteristics are presented in Table 1. In this table, all percentages are expressed in mass.

TABLE 1

Characteristics of the fuel oil

| CHARACTERISTICS | STANDARDS/ METHODS | UNITS | RESULTS |
|---|---|---|---|
| Density at 15° C. | NF T 60-172 ASTM D4052 | $Kg/m^3$ | 1018.4 |
| Viscosity at 50° C. | NF T 60-100 ASTM D445 | $mm^2/s$ | 527.88 |
| Viscosity at 100° C. | NF T 60-100 ASTM D445 | $mm^2/s$ | 39.09 |
| Carbon | | % | 84.45 |
| Kjeldahl nitrogen | ASTM D3228 | % | 0.44 |
| Hydrogen | | % | 9.81 |
| Sulfur | | % | 2.72 |
| Measured HHV | | MJ/kg | 41.84 |
| Calculated LHV | | MJ/kg | 39.76 |
| Asphaltenes | NFT60-115 IP 143 | % | 7.6 |
| Conradson carbon residue | ASTM D4530 | % | 14.4 |
| Ashes | NF M 07-045 IN ISO 6245 | % | 0.039 |
| Insolubles | NF M 07-063 | Ppm | 250 |
| Total metals | Atomic emission | Ppm | 240 |

The process conditions are very much identical for all three tests and are grouped together in Table 2.

TABLE 2

Process conditions

| CHARACTERISTICS Total concentration in metals brought by the additives | Test A (without additive) 0 | | | Test B (+ bimetallic additive) 40 | | | Test C (+ trimetallic additive) 40 | | |
|---|---|---|---|---|---|---|---|---|---|
| (in ppm in relation to the fuel) | A1 | A2 | A3 | B1 | B2 | B3 | C1 | C2 | C3 |
| Total oxygen (%) | 3.1 | 2.2 | 1.4 | 3.4 | 2.4 | 1.7 | 3.0 | 2.1 | 1.4 |
| Fuel oil flow (kg/h) | 516 | 515 | 514 | 504 | 516 | 510 | 515 | 510 | 512 |
| Fuel oil pressure ($10^5$ Pa) | 8.0 | 7.9 | 8.0 | 7.8 | 7.8 | 7.8 | 7.8 | 7.7 | 7.9 |
| Fuel oil temp. (° C.) | 74 | 74 | 75 | 75 | 74 | 75 | 75 | 75 | 75 |
| Fuel oil viscosity ($mm^2/s$) | 125 | 120 | 120 | 120 | 125 | 120 | 120 | 120 | 120 |
| Pulv. Air. Pressure ($10^5$ Pa) | 6.2 | 6.2 | 6.0 | 6.0 | 5.9 | 6.1 | 6.1 | 6 | 6.1 |
| Pulv. Air. Temp. (° C.) | 23 | 23 | 23 | 25 | 25 | 25 | 23 | 24 | 24 |

For each test and for each of the three combustion excess air values, we complete an isokinetic sampling and a weight determination of the solid unburned components produced during the combustion, as well as analyses of the combustion gases. For measurement needs, the unburned components are drawn at the chimney in a steady flow area, at a height of approximately 5 meters.

These measurements or analyses are completed at least one hour after the beginning of the injection of each of the two additives, the boiler being fed for at least one hour with the fuel containing no additives between each of the tests.

The results of the measurements and analyses will be provided in Table 3.

TABLE 3

Measurements of the unburned components and analyses of the combustion gases

| Total concentration in metals Brought by the additives (in ppm in relation to the fuel) | Test A (without additives) 0 | | | Test B (+ bimetallic additive) 40 | | | Test C (+ trimetallic additive) 40 | | |
|---|---|---|---|---|---|---|---|---|---|
| | A1 | A2 | A3 | B1 | B2 | B3 | C1 | C2 | C3 |
| Total oxygen (%) | 3.2 | 2.2 | 1.4 | 3.5 | 2.5 | 1.7 | 3.0 | 2.1 | 1.4 |
| Solid unburned components (mg/Nm3 at 3% of $O_2$) | 129 | 234 | 348 | 88 | 144 | 247 | 90 | 152 | 245 |
| Calculated $CO_2$(%) | 13.3 | 14.1 | 14.7 | 13.2 | 13.9 | 14.5 | 13.5 | 14.1 | 14.8 |
| CO (ppm) | 3 | 5 | 13 | 2 | — | — | 0 | 0 | 7 |
| NOX (ppm) | 352 | 333 | 314 | 342 | 335 | 313 | 345 | 325 | 313 |
| NOX (mg/Nm3 at 3% of $O_2$) | 746 | 658 | 600 | 750 | 674 | 603 | 719 | 653 | 593 |

FIG. 1 of the attached illustrations represents in a graphical manner the variations of the quantities of solid unburned components (mg/Nm$^3$ at 3% of $O_2$) during each of the three tests, in relation to the content in combustion oxygen (%).

Figure 2:
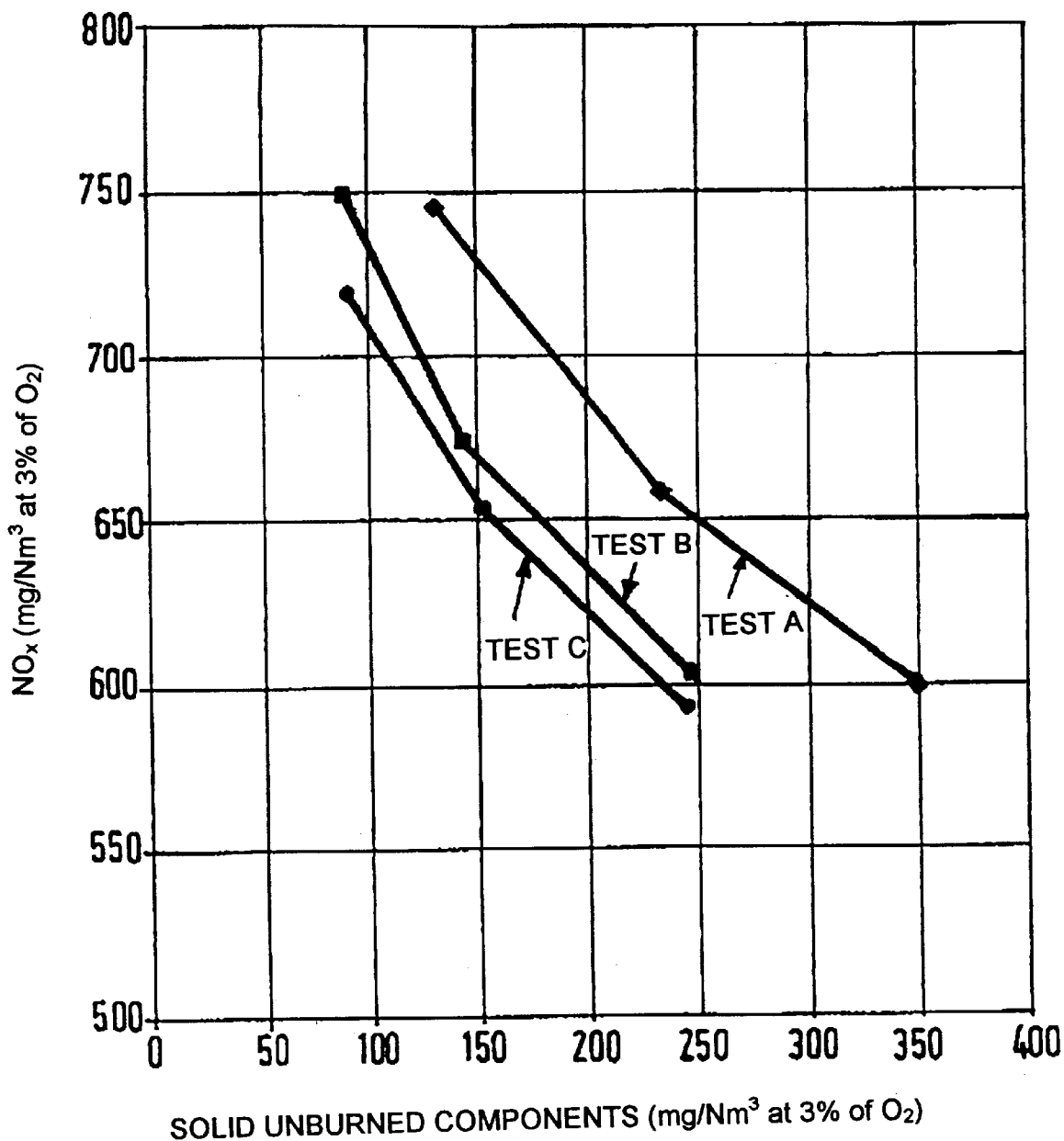

In the same way, FIG. 2 is a graphical representation of the variations of nitrogen oxides (mg/Nm$^3$ at 3% of $O_2$) measured, in relation to the unburned products during the combustion.

In FIG. 1, we can see that for a constant oxygen content, the presence of an additive in the combustion fuel oil makes it possible to appreciably reduce the quantities of unburned components during said combustion.

The trimetallic additive (test C) that is the object of this invention, present in a fuel gas with a content of 40 ppm, allows:

to reduce the quantity of solid unburned components by approximately 30% to approximately 35% compared with a same fuel gas without the additive (test A), when the oxygen content of the smoke varies appreciably from 1.5% to 3.0%. This reduction in unburned components is of approximately 20% for the bimetallic additive (test B).

to improve by approximately 50% the performances obtained with the bimetallic additive whose composition is described in EP-B-112 219.

Furthermore, in FIG. 1, we note that for a same target of quantity of solid unburned components, the presence of the trimetallic additive allows for the boiler to operate with less excess air.

The quantity of nitrogen oxides produced during a combustion being proportional to the excess air of said combustion, the trimetallic additive that is the object of this invention allows for the indirect reduction of the quantities of nitrogen oxides produced during the combustion of a fuel oil to which the composition that is the object of this invention has been added.

FIG. 2 illustrates that for a same content of solid unburned components, the use of the trimetallic additive (test C) allows for the reduction of the emission of nitrogen oxides by approximately 10% when compared with the combustion of a same fuel gas without the additive.

Furthermore, the trimetallic additive makes it possible to limit the emission of unburned components to very low values (between 50 and 100 mg/Nm$^3$ at 3% of $O_2$) without the costly and constraining recourse to complicated dust collectors.

The use of the trimetallic additive that is the object of this invention makes it possible to attain a better compromise between the emissions of the solid unburned components and those of the nitrogen oxides.

The performance of the combustion plants can therefore be improved by:

a reduction of the excess air, therefore of the nitrogen oxides produced during said combustion, a reduction of the losses in smoke by reduction of the solid unburned components, a reduction of the clogging of the exchange surfaces.

Furthermore, the operating cost can also be reduced due to fewer sweepings, cleanings and disposals on land of soot caught for example in the dust collectors.

What is claimed is:

1. A mixed organometallic composition comprising organic acid salts of at least three metals M1, M2 and M3, wherein M1 is selected from the group consisting of at least one metal belonging to either the iron group or the manganese group, M2 is selected from the group consisting of at least one metal belonging to the rare earth metal group, M3 is selected from the group consisting of at least one metal belonging to the alkaline or the alkaline earth group, and wherein the R ratio of the mass contents of metals M3/M2, is greater than 0.15.

2. The composition as set forth in claim 1, wherein said M2 is a metal selected from the group consisting of cerium, lanthanum, neodymium and praseodymium.

3. The composition as set forth in claim 1, wherein said M3 is a metal selected from the group consisting of barium, strontium, calcium and lithium.

4. The composition as set forth in claim 1, wherein said composition comprises, in relation to the total weight of the metals, at least 30% by weight of the M1 metal and at least 10% by weight of the M2 metal.

5. The composition as set forth in claim 1, wherein the organic acid is selected from the group consisting of fatty acids that have more than 7 carbon atoms.

6. The composition as set forth in claim 5, wherein the organic acid salts are salts of alkyl, aryl, or alkylaryl sulfonic acids or carboxylic acids with an alkylaryl chain containing more than 8 carbon atoms.

7. The composition as set forth in claim 1, wherein said organic acid salts are diluted in an organic solvent.

8. The composition as set forth in claim 1, wherein said M1 is a metal selected from the group consisting of iron, manganese, cobalt and nickel.

9. The composition as set forth in claim 8 wherein the M1 element is iron.

10. The composition as set forth in claim 2, wherein the M2 element is cerium.

11. The composition as set forth in claim 3, wherein the M3 element is calcium.

12. The composition as set forth in claim 1, wherein the R ratio of the mass contents of metals M3/M2, is greater than 1.5.

13. The composition as set forth in claim 7, wherein the organic solvent is of the aromatic type.

14. The composition as set forth in claim 13 wherein the organic solvent comprises aromatic molecules in an amount greater than 50% by weight.

15. The composition as set forth in claim 14, wherein the organic solvent comprises aromatic molecules in an amount greater than 80% by weight.

16. A hydrocarbon fuel or motor fuel comprising as an additive a mixed organometallic composition comprising organic acid salts of at least three metals M1, M2 and M3, wherein M1 is selected from the group consisting of at least one metal belonging to either the iron group or the manganese group, M2 is selected from the group consisting of at least one metal belonging to the rare earth metal group, M3 is selected from the group consisting of at least one metal belonging to the alkaline or the alkaline earth group, and wherein the R ratio of the mass contents of metals M3/M2, is greater than 0.15.

17. The hydrocarbon fuel or motor fuel as set forth in claim 16, wherein said fuel comprises greater than 10 ppm of said additive composition, based on the total concentration in added metals of the additive composition.

18. The hydrocarbon fuel or motor fuel as set forth in claim 17, wherein said fuel comprises greater than 40 ppm of said additive composition, based on the total concentration in added metals of the additive composition.

19. The hydrocarbon fuel or motor fuel as set forth in claim 16, wherein said M1 is a metal selected from the group consisting of iron, manganese, cobalt and nickel.

20. The hydrocarbon fuel or motor fuel as set forth in claim 19, wherein said M1 is iron.

21. The hydrocarbon fuel or motor fuel as set forth in claim 16, wherein said M2 is a metal selected from the group consisting of cerium, lanthanum, neodymium and praseodymium.

22. The hydrocarbon fuel or motor fuel as set forth in claim 21, wherein said M2 is cerium.

23. The hydrocarbon fuel or motor fuel as set forth in claim 16, wherein said M3 is a metal selected from the group consisting of barium, strontium, calcium and lithium.

24. The hydrocarbon fuel or motor fuel as set forth in claim 23, wherein said M3 is calcium.

25. The hydrocarbon fuel or motor fuel as set forth in claim 16, wherein the R ratio of the mass contents of metals M3/M2, is greater than 1.5.

26. The hydrocarbon fuel or motor fuel as set forth in claim 16, wherein said composition comprises, in relation to the total weight of the metals, at least 30% by weight of the M1 metal and at least 10% by weight of the M2 metal.

27. The hydrocarbon fuel or motor fuel as set forth in claim 16, wherein the organic acid is selected from the group consisting of fatty acids that have more than 7 carbon atoms.

28. The hydrocarbon fuel or motor fuel as set forth in claim 27, wherein the organic acid salts are salts of alkyl, aryl, or alkylaryl sulfonic acids or carboxylic acids with an alkylaryl chain containing more than 8 carbon atoms.

29. The hydrocarbon fuel or motor fuel as set forth in claim 16, wherein said organic acid salts are diluted in an organic solvent.

30. The hydrocarbon fuel or motor fuel as set forth in claim 29, wherein the organic solvent is of the aromatic type.

31. The hydrocarbon fuel or motor fuel as set forth in claim 30, wherein the organic solvent comprises aromatic molecules in an amount greater than 50% by weight.

32. The hydrocarbon fuel or motor fuel as set forth in claim 31, wherein the organic solvent comprises aromatic molecules in an amount greater than 80% by weight.

* * * * *